United States Patent [19]

Saville

[11] Plant 5,089

[45] Aug. 23, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 382,589

[22] Filed: May 27, 1982

[51] Int. Cl.[3] ..... A01H 5/00

[52] U.S. Cl. ..... Plt./7

[58] Field of Search ..... Plt./7

*Primary Examiner*—James R. Feyrer

*Attorney, Agent, or Firm*—Vincent G. Gioia

[57] ABSTRACT

A new miniature rose variety of brick red to carrot red colored flowers.

1 Drawing Figure

The present invention relates to a new and distinct variety of rose plant of the miniature rose class, which was originated by my crossing as seed parent my seedling of (Sheri Anne×Glenfiddich) and as pollen parent my seedling of [(Sarabande×Little Chief)×unknown moss seedling]. The denomination of this new rose is "Savswet".

Among the novel characteristics possessed by this new variety which distinguish it from its parents and all other varieties of which I am aware are decorative brick red to carrot red colored flowers on a vigorous but low growing plant. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "35C" is plate 35C of The Royal Horticultural Society Colour Chart.

Parentage: Seedling.

*Seed parent.*—My unpatented, unreleased seedling of (Sheri Anne×Glenfiddich).

*Pollen parent.*—My unpatented, unreleased seedling of [(Sarabande×Little Chief)×Unknown moss seedling].

Class: Miniature.

The following observations are made of specimens grown under glass in Essex County, Mass. during the month of March.

FLOWER

Blooming habit: Continuous.

A. Bud:

(1) *Size.*—Small.

(2) *Form.*—Ovoid.

(3) *Color.*—After sepals divide, 35C to 33D.

(4) *Sepals.*—Ordinary, slightly longer than bud.

(5) *Peduncle.*—Length — about ½ to ¾ inch. Aspect — straight. Strength — erect. Color — near 145A.

B. Bloom:

(1) *Size.*—Average size when fully expanded — about 1 inch.

(2) *Borne.*—Singly and sprays.

(3) *Form.*—Decorative, globular.

(4) *Petalage.*—Number of petals under normal conditions — about 25.

(5) *Color.*—As buds open and petals unfurl, brick red coloring continues however, outer petals lighten and outer petal segments show some azalea pink 39D tones. Concentration of petal coloring at flower centers before opening show deeper brick red tonality. Yellow coloring toward point of petal attachment may be seen in open blooms. Overall tonality upon aging viewed from a distance is carrot red 29B to 29C.

C. Petals:

(1) *Texture.*—Thick.

(2) *Appearance.*—Inside velvety, outside satiny.

(3) *Form.*—Fan shaped with apices.

(4) *Arrangement.*—Regularly arranged, shingle-like.

(5) *Petaloids in center.*—Few.

(6) *Persistence.*—Drop off cleanly.

(7) *Fragrance.*—Slight.

(8) *Lasting quality.*—Good lasting on plant and as cut flower.

REPRODUCTIVE ORGANS

A. Stamens, filaments and anthers:

(1) *Arrangement.*—Stamens regularly arranged around styles.

(2) *Color.*—Near 17A.

B. Pollen:

*Color.*—Near 21A.

C. Styles: Even, medium length.

D. Stigmas:

*Color.*—Near 157D.

E. Hips: None observed.

PLANT

A. Form: Compact, bushy.

B. Growth: Vigorous, uniform branching, low growing.

*Height attained.*—About 8 inches.

C. Foliage: Compound 5 to 7 leaflets.

(1) *Size.*—Small.

(2) *Quantity.*—Abundant.

(3) *Color.*—New foliage: Upper side — near to 137B; Under side — near to 139A. Old foliage: Upper side — near to 137A; Under side — near to 147B.

(4) *Shape.*—Oval.

(5) *Texture.*—Upper side is slightly glossy and under side is matte.

(6) *Edge.*—Serrated.

(7) *Serration.*—Small.

(8) *Leaf stem.*—Color — near to 144A. Under side — near 144B.

(9) *Stipules.*—Medium.

(10) *Resistance to disease.*—Blackspot — average. Mildew — average. Rust — average.

D. Wood:

(1) *New wood.*—Color — near 146C. Bark — smooth.

(2) *Old wood.*—Color — near 146A. Bark — smooth.

E. Thorns:

(1) *Thorns.*—Quantity (main stalk) — few. On laterals from stalk — none. Form — straight, thin, slightly downward slanting. Length — short. Position — scattered.

(2) *Prickles.*—None.

F. Winter hardiness: Needs protection in severe climate.

I claim:

1. A new and distinct variety of rose plant of the miniature rose class, substantially as shown and described, characterized particularly by brick red to carrot red colored flowers borne on a vigorous but low growing plant.

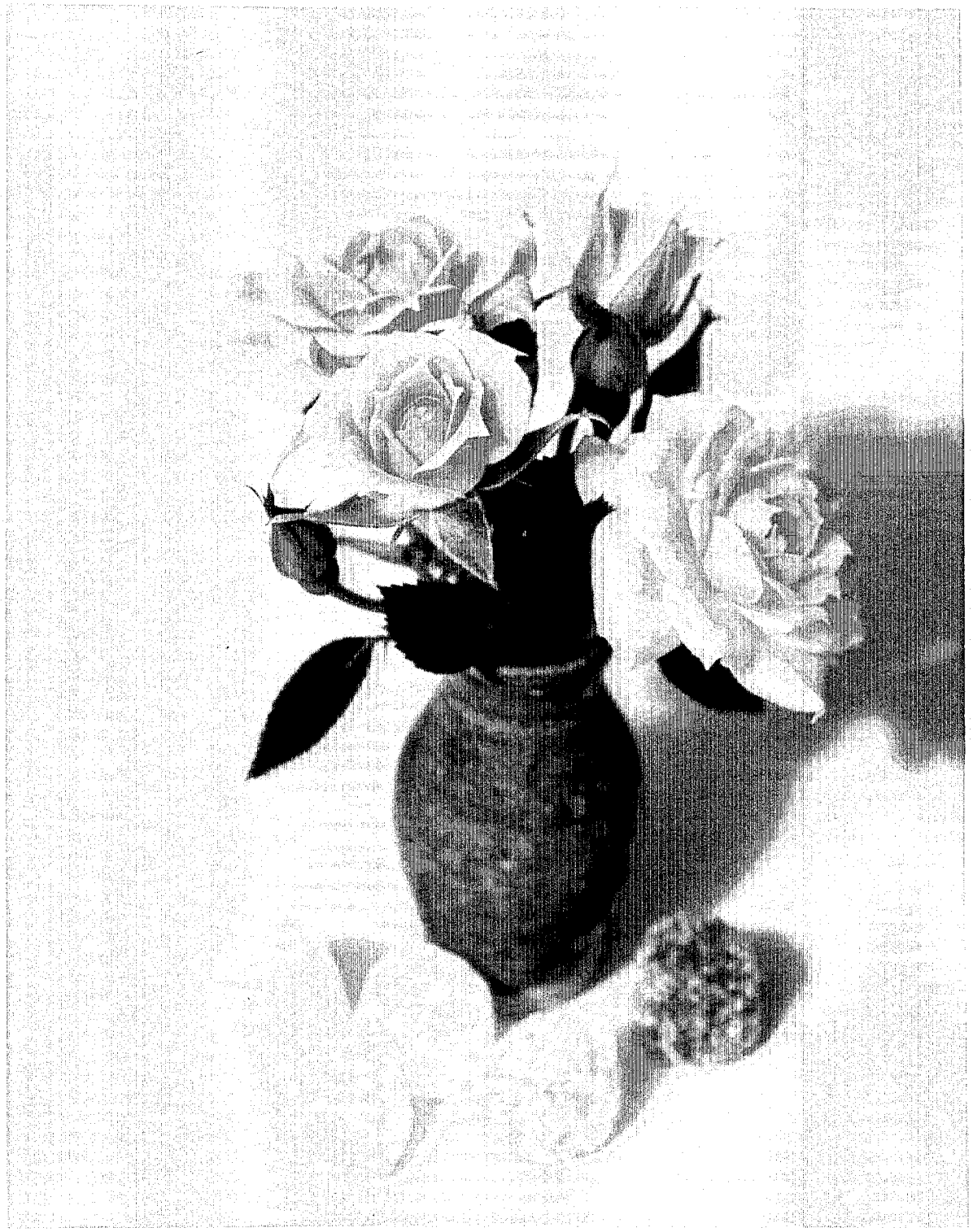

* * * * *